US009409832B2

(12) United States Patent
Lefenfeld et al.

(10) Patent No.: US 9,409,832 B2
(45) Date of Patent: Aug. 9, 2016

(54) CATALYTIC DEHYDRATION OF ALCOHOLS USING NON-VOLATILE ACID CATALYSTS

(71) Applicant: SIGNA CHEMISTRY, INC., New York, NY (US)

(72) Inventors: Michael Lefenfeld, New York, NY (US); Robert Hoch, Hensonville, NY (US)

(73) Assignee: SIGNA CHEMISTRY, INC., New York, NY (US)

( * ) Notice: Subject to any disclaimer, the term of this patent is extended or adjusted under 35 U.S.C. 154(b) by 0 days.

(21) Appl. No.: 14/662,744

(22) Filed: Mar. 19, 2015

(65) Prior Publication Data

US 2015/0307413 A1    Oct. 29, 2015

Related U.S. Application Data

(63) Continuation of application No. 13/497,627, filed as application No. PCT/US2010/043650 on Jul. 29, 2010, now Pat. No. 9,040,741.

(60) Provisional application No. 61/245,532, filed on Sep. 24, 2009, provisional application No. 61/366,923, filed on Jul. 22, 2010.

(51) Int. Cl.
*C07C 33/00* (2006.01)
*C07C 1/24* (2006.01)

(52) U.S. Cl.
CPC ............. *C07C 1/24* (2013.01); *C07C 2529/40* (2013.01); *C07C 2529/83* (2013.01); *C07C 2529/84* (2013.01); *C07C 2529/85* (2013.01)

(58) Field of Classification Search
CPC .......... C07C 33/00; C07C 1/24; C07C 11/04; C07C 11/02; C07C 2529/40; C07C 2529/83
USPC ................................................. 560/129, 212
See application file for complete search history.

(56) References Cited

U.S. PATENT DOCUMENTS

| 2,967,897 A | 1/1961 | Sharp et al. |
| 4,396,789 A | 8/1983 | Barrocas et al. |

(Continued)

FOREIGN PATENT DOCUMENTS

| EP | 0 712 824 A1 | 5/1996 |
| WO | 88/02361 A1 | 4/1988 |

(Continued)

OTHER PUBLICATIONS

International Search Report and Written Opinion of International Application No. PCT/US2010/043650, dated Sep. 16, 2010.

(Continued)

*Primary Examiner* — Kamal Saeed
*Assistant Examiner* — Janet L Coppins
(74) *Attorney, Agent, or Firm* — J.A. Lindeman & Co., PLLC

(57) ABSTRACT

A catalytic process for dehydration of an aliphatic $C_2$-$C_6$ alcohol to its corresponding olefin is disclosed. The process continuously flows through a reaction zone a liquid phase containing an aliphatic $C_2$-$C_6$ alcohol to contact a non-volatile acid catalyst at a reaction temperature and pressure to at least partially convert the aliphatic $C_2$-$C_6$ alcohol in the liquid phase to its corresponding olefin. The reaction pressure is greater than atmospheric pressure and the reaction temperature is above the boiling point of the olefin at reaction pressure, but below the critical temperature of the alcohol, and the olefin product is substantially in the gaseous phase. After the contacting step, the olefin containing gaseous phase is separated from the liquid phase. The invention also relates to catalytic processes such as a hydrolysis of an olefin to an alcohol, an esterification, a transesterification, a polymerization, an aldol condensation or an ester hydrolysis.

16 Claims, 1 Drawing Sheet

(56) References Cited

U.S. PATENT DOCUMENTS

2007/0287873 A1* 12/2007 Coupard et al.
2009/0062580 A1   3/2009 Takai et al.

FOREIGN PATENT DOCUMENTS

| WO | WO 88/02361 | * | 4/1988 | ............... C07C 69/52 |
| WO | WO-98/02361 A1 | * | 4/1998 | |
| WO | 2009/098262 A1 | | 8/2009 | |
| WO | 2011037681 A1 | | 3/2011 | |

OTHER PUBLICATIONS

Campelo, J.M. et al.: "Converting Reaction of Alcohols (alpha-methylated) on Aluminum Phosphate Catalyst," Chemistry and Adhesion, No. 1, 1996, pp. 54-57.

English Translation of Campelo, J.M. et al.: "Converting Reaction of Alcohols (alpha-methylated) on Aluminum Phosphate Catalyst," Chemistry and Adhesion, No. 1, 1996, pp. 54-57.

* cited by examiner

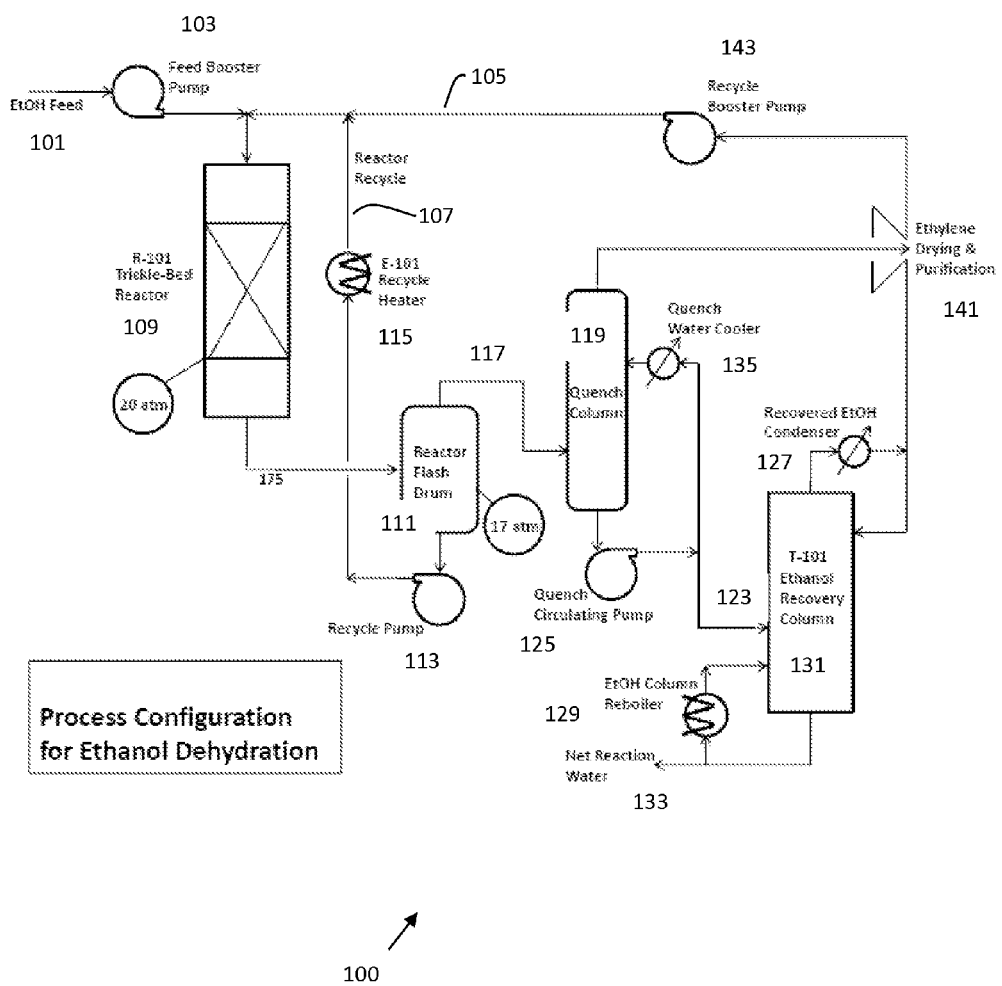

CATALYTIC DEHYDRATION OF ALCOHOLS USING NON-VOLATILE ACID CATALYSTS

CROSS REFERENCE TO RELATED APPLICATIONS

This application is a continuation application of U.S. patent application Ser. No. 13/497,627, filed on May 14, 2012, which is a U.S. National Phase application of PCT Application No. PCT/US2010/043650, filed on Jul. 29, 2010, which claims priority to U.S. application 61/245,532, filed Sep. 24, 2009, and to U.S. application 61/366,923, filed Jul. 22, 2010, all of which are incorporated herein by reference in their entirety.

FIELD OF THE INVENTION

The invention relates to acid-catalyzed reactions, such as the dehydration of numerous oxygenated compounds to form their respective olefin.

BACKGROUND OF THE INVENTION

Olefins, (exemplified herein as, but not limited to, ethylene, propylene, butenes, and mixtures thereof), and their substituted counterparts, serve as feedstocks for the production of numerous chemicals and polymers. For example, ethylene is one of the largest volume chemical intermediates in the world, being used as a raw material in the production of, for example, polyethylene, ethylbenzene-styrene, ethylene dichloride, ethylene oxide and ethylene glycol. Most olefins are commercially produced by the thermal or catalytic cracking of saturated hydrocarbons found in petroleum and naphtha (See M. Ladisch et al., Science (1979) 205, 898). Due to the thermodynamic limitations of the reaction, thermal cracking reactors operate at temperatures as high as 1,100° C., and challengingly short reaction times, to maintain the desired levels of conversion—typical yields are between 50 and 100% (See U.S. Patent Applications and Patents: 2006/0149109; U.S. Pat. Nos. 4,351,732; 4,556,460; 4,423,270; and 4,134,926). Information on production of ethylene by thermal cracking is available in *Kirk Othmer Encyclopedia of Chemical Technology*, 5$^{th}$ ed. Wiley (2004-2007), and *Ullmann's Encyclopedia of Industrial Chemistry*, 6$^{th}$ ed. Wiley (2003), both of which are hereby incorporated by reference.

Finding new, more efficient, and environmentally friendly pathways to produce olefins from renewable starting materials that are not encumbered by the varying costs and tightening supply of crude petroleum has been a challenging research area of the past decade (See U.S. Patent Applications and Patents: 2006/0149109; U.S. Pat. Nos. 4,351,732; 4,556,460; 4,423,270; and 4,134,926). Lower alcohols, such as ethanol, propanol, and butanol, are frequently available from renewable sources and thus provide a pathway to their corresponding olefins independent of fossil fuels. Catalytic oxidative dehydration of ethane was proposed as an alternative method to produce ethylene at much lower temperatures, but the yields and selectivity achieved to date have not been encouraging (See S. Golay et al., Chem. Eng. Sci. (1999) 54, 3593).

The dehydration of oxygenates, such as alcohols, can be carried out using liquid acids, either concentrated sulfuric acid or concentrated phosphoric acid, $H_3PO_4$, as a catalyst. The mechanistic details for the dehydration reaction can be summarized in Scheme 1 (below). The alcohol is first protonated, followed by a loss of water to give a carbocation (carbonium ion), which results in the subsequent abstraction of a hydrogen ion from the carbocation. Apart from the acid's corrosive nature, as a side reaction, the acid can oxidize the alcohol into polluting carbon dioxide. Also, in the case of concentrated $H_2SO_4$, large quantities of sulfur dioxide can be produced. Both of these gases have to be removed from the product olefin before it can be used in a later chemical process.

Scheme 1. Mechanism for the Acidic Dehydration of Alcohols

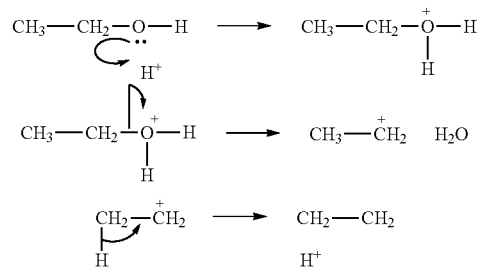

Silicoaluminophosphates (SAPOs), such as SAPO-34 and its analogues, possess strong Brönsted acid sites and are excellent shape-selective catalysts for the conversion of methanol and other alcohols to light olefins (See U.S. Pat. Nos. 4,499,327; 5,952,538; 6,046,673; 6,334,994; and 7,199,277; as well as WO 1993/024430). However, SAPOs are composed of Si atoms tetrahedrally coordinated to oxygen atoms making an integral part of the overall catalyst framework. SAPO-34 is being commercially exploited (by UOP) for the selective conversion of methanol to low-molecular weight olefins (See WO 2007/032899). Further, the Brönsted acidity of a silicoaluminophosphate varies greatly depending on its particular structure type and architecture.

Olefins, particularly light olefins, are the most desirable products from oxygenate conversion and crude petroleum cracking. A need exists to improve the performance of ethylene and propylene plants. To this end, a number of catalytically mediated processes have been proposed. The most chemically straightforward among these is ethanol, or propanol, dehydration.

Many of the downstream industrial processes for which ethylene is the raw material, including the manufacture of polyethylene, ethylene dichloride, ethylene oxide, etc. operate at super atmospheric pressure. Processes for dehydration of ethanol to ethylene are well known. These processes typically require temperatures in excess of 300° C. where both the olefin and alcohol are in the gas phase and achieve essentially complete conversion of alcohol to olefin. The thermodynamics, however, favor such high alcohol to olefin conversions only at low pressure, so the process is conventionally operated at or just above atmospheric pressure. The ethylene produced must also meet critical purity specifications. Purification is conventionally done via cryogenic distillation at elevated pressure. Thus, if ethylene is produced by the conventional gas phase dehydration of ethanol, it must be compressed before purification. Moreover, ethylene produced from an ethanol dehydration unit must, after purification, again be compressed to the operating pressure of the eventual downstream process. Clearly, there is a need to produce ethylene by ethanol, or propylene by propanol, dehydration at elevated pressure such that its downstream use avoids such steps and becomes more economical.

In addition, renewable ethanol, a potential dehydration feedstock, is typically made by fermentation of an agricultural material in an aqueous medium. The ethanol after being separated from fermentation solids is quite dilute in water. Most of this water is conventionally removed from the fermentation broth before dehydration to form ethylene. The presence of water is thermodynamically detrimental to achieving a high conversion in gas phase dehydration. There exists, therefore, a need for a dehydration process capable of accepting aqueous ethanol as its feedstock.

BRIEF DESCRIPTION OF THE FIGURE

FIG. 1 shows a process configuration for ethanol dehydration.

SUMMARY OF THE INVENTION

The invention relates to a process for the catalytic dehydration of alcohols to form olefins. The process contacts a liquid feedstock containing an alcohol with a non-volatile acid catalyst under conditions sufficient to convert the alcohol to an olefin and recovers the olefin produced as a gas.

The invention relates to a catalytic process for dehydration of an aliphatic $C_2$-$C_6$ alcohol to its corresponding olefin. The process continuously flows, through a reaction zone, a liquid phase containing an aliphatic $C_2$-$C_6$ alcohol to contact a non-volatile acid catalyst at a reaction temperature and pressure to at least partially convert the aliphatic $C_2$-$C_6$ alcohol in the liquid phase to its corresponding olefin. The reaction pressure is greater than atmospheric pressure and the reaction temperature is above the boiling point of the olefin at reaction pressure, but below the critical temperature of the alcohol, and the olefin product is substantially in the gaseous phase. The process then separates the olefin containing gaseous phase from the liquid phase.

In one the embodiment, a process of the invention has the additional steps of: recovering at least a portion of the liquid phase as a reaction effluent; recovering any unconverted aliphatic $C_2$-$C_6$ alcohol from the olefin-containing gaseous phase or from the reaction effluent; and recycling any unconverted alcohol to the reaction zone.

While a process of the invention is generally described with reference to the dehydration of alcohols to form olefins, as another embodiment the process of the invention may also be used in reactions such as the hydrolysis of olefins to alcohols, esterification, transesterification, polymerization, aldol condensation and ester hydrolysis. Accordingly, the invention also relates to catalytic processes for the conversion of an alcohol, an olefin, an aldehyde, a ketone or an ester where the catalytic process is a hydrolysis of an olefin to an alcohol, an esterification, a transesterification, a polymerization, an aldol condensation or an ester hydrolysis.

DETAILED DESCRIPTION OF THE INVENTION

It has now been found that dehydrating an alcohol, such as ethanol, in the liquid phase while simultaneously removing the corresponding olefin produced, e.g. ethylene, as a gas, permits operation of the reaction zone at elevated pressure and further allows the use of dilute ethanol as feedstock. In order for the alcohol to be in the liquid phase, the reaction temperature must be below the critical temperature of the alcohol. The term "critical temperature" is used here in its classical thermodynamic sense, the temperature above which the compound cannot be liquefied at any pressure. See, for example, *Lange's Handbook of Chemistry*, Thirteenth Edition, page 9-181. Table 9-7 of this handbook provides a list of critical temperatures as does: Lydersen, A. L. and Tsochev, V., Chem. Eng. Technol. 13 (1990) 125-130. The critical temperature (Tc) and critical pressure (Pc) of some exemplary alcohols and olefins are listed in Table 1 below. Operation at these lower temperatures, in turn, requires a catalyst with sufficient activity at that temperature to effect the dehydration reaction with commercially viable rates.

Although elevated reaction pressures have advantages, it will be appreciated that the higher the pressure, the higher the equilibrium olefin concentration in the liquid phase. These higher liquid phase olefin concentrations, in turn, can promote olefin polymerization with concomitant loss in yield. Thus, especially with olefins higher than $C_2$ and $C_3$, operation at higher pressure than needed to facilitate downstream purification is undesirable.

TABLE 1

| Compound | $T_C$ (° C.) | $P_C$ (atm) |
| --- | --- | --- |
| Ethanol | 243 | 63 |
| Ethylene | 9.2 | 49.7 |
| Propanol | 264 | 51 |
| Propylene | 91.8 | 45.6 |
| N-butanol | 290 | 43.6 |
| Butene-1 | 146 | 39.7 |
| Cis-Butene-2 | 162 | 41.5 |
| Trans-Butene-2 | 155 | 40.5 |
| Isobutanol | 274 | 42.4 |
| Isobutylene | 145 | 39.5 |
| T-butanol | 233 | 39.2 |
| 1-pentanol | 313 | |
| Pentene-1 | 192 | 40 |
| Pentene-2 | 203 | 36 |
| 1-hexanol | 337 | |
| Hexene-1 | 231 | |

Accordingly, the invention relates to a process for the catalytic dehydration of alcohols to form olefins. The process contacts a liquid feedstock containing an alcohol with a non-volatile acid catalyst under conditions sufficient to convert the alcohol to an olefin and recovers the olefin produced as a gas. The process of the invention is particularly useful in converting "light alcohols" to their corresponding "light olefins."

FIG. 1 illustrates a typical process configuration 100 for practice of the invention for dehydration of an alcohol, e.g. ethanol, continuously at an industrial scale. (It should be understood that a number of equipment items such as drums and pumps not critical to understanding the process have been omitted from FIG. 1.) Feed ethanol 100, which may be conveniently supplied as its water azeotrope (ca. 5 wt % water) is fed to the process, such as through feed booster pump 103. Feed ethanol 101 is compressed to reaction pressure and combined with recycle streams 105, 107 before entering the top of a trickle bed reactor 109. Initially, only liquid contacts the catalyst, but as soon as ethylene is produced by reaction, three phase conditions exist. The reactor 109 operates in co-current downflow over a solid catalyst which may be configured in one or more beds within the reactor 109. Although heat may be supplied directly to the reactor 109, heat of reaction, is more conveniently supplied by for example by heating the feedstock and/or permitting a modest cooling of the reaction mass.

Reactor effluent 175 is flashed in reactor flash drum 111 to separate the liquid and vapour phases. The liquid phase is recycled to the reactor 109 via recycle pump 113 and through a heat exchanger 115, which supplies the heat of reaction in the form of latent heat to the liquid stream 107. Gas phase product 117, containing essentially all the ethylene is fed to a quench system such as quench column 119 to remove any acid or other water soluble impurities, including diethyl ether, as well as unconverted ethanol. The scrubber liquid may be mildly basic to facilitate recovery of acids. Ethylene 123 from the scrubber can be fed forward to a conventional drying and purification system 141.

Desirably, at least one mole of water per mole of ethylene produced remains in the vapor phase after the flash. If this is not the case, (depending on reaction conditions and catalyst performance), a slipstream of flash bottoms is diverted (not shown) and added to the purge 121 from the quench loop. This stream 123 (which may be supplemented by the aforementioned slipstream) is fed via quench circulating pump 125 to an ethanol recovery column 131 which recovers any ethanol present as the water azeotrope for recycle to the reactor 109. Bottoms from the ethanol recovery column 131 comprise the net water 133 that needs to be rejected from the process, one mole per mole of olefin made plus any water associated with by-products plus any water contained in the ethanol feed. Recovered ethanol condenser 127, ethanol column re-boiler 129, quench water cooler 135, and booster pump 143 can be incorporated as shown to facilitate the process. Alternative process configurations are, of course, feasible and are within the scope of the invention.

Prior art processes for liquid phase dehydration of alcohols to olefins, with olefin withdrawal as a vapour, such as described in U.S. Pat. No. 3,526,674, were designed to minimize contact of the product olefin with the catalyst in order to reduce undesirable oligomerization reactions. Thus, these processes were applicable to olefins capable of existing in the liquid phase at reaction temperature, i.e. at reaction temperatures below the critical temperature of the olefin. There was also no motivation to operate such prior art processes at pressures above atmospheric. Not only would higher pressures adversely affect the reaction equilibrium, such pressures would reduce the volatility of the olefin making gas phase removal more difficult.

The terms "lower alcohols" or "lower olefins" refers to alcohols and olefins having two to six carbon atoms, inclusive. Although other hydrocarbon products are formed, the products of particular interest herein are the corresponding light olefins and they are preferably produced as the major hydrocarbon products i.e., over 50 mole percent of the hydrocarbon product is light olefins. Examples of alcohol dehydration include: conversion of lower alkanols to their corresponding olefins, especially ethanol to ethylene, propanol to propylene and t-butyl alcohol to isobutylene This process is useful for aliphatic alcohols containing two to six carbon atoms per molecule. Although the process can be applied to olefins and to prepare their corresponding alcohols having more than six carbon atoms, the olefins corresponding to these alcohols generally do not require a high pressure cryogenic purification train and thus the benefit of liquid phase operation is significantly reduced. The process is preferably applied to form alcohols having two to five carbon atoms per molecule, more preferably applied to alcohols having two to four carbon atoms per molecule and even more preferably applied to alcohols having two or three carbon atoms per molecule.

A non-volatile acid catalyst is used in a process of the invention. The non-volatile acid is preferably a solid acid catalyst. Solid acid catalysts useful in the invention include isomorphously substituted aluminum phosphate (AlPO) catalysts such as disclosed in PCT/US10/021882, filed Jan. 22, 2010, and published on Jul. 29, 2010 as WO/2010/085708. (incorporated herein by reference). Unsubstituted AlPO's may also be employed; see U.S. Pat. No. 3,915,893 and Campelo, J. M., et al. J. Catalysis 151 (1995) 307-314. Other strong solid acids such as SAPO's, silicalites, and zeolites may also be employed. Zeolite ZSM-5, (see U.S. Pat. Nos. 3,702,886 and 4,100,262) is of particular interest because it has been shown, [Phillips and Datta (IEC Res 1997 36 4466-4475)], to convert ethanol to ethylene in the vapour phase. Other non-volatile acids known in the art, such as sulphuric acid, p-toluenesulfonic acid, methanesulfonic acid, heteropoly acids or phosphoric acid may also be used in the processes of the invention. The reaction is carried out with the alcohol, like ethanol, in the liquid phase, such that it is contacted in a reaction zone with a non-volatile acid catalyst at effective process conditions such as to produce light olefins in the gas phase, i.e., an effective temperature, pressure, Weight Hourly Space Velocity (WHSV), and, optionally, an effective amount of diluent, correlated to produce light olefins.

The isomorphously substituted AlPO catalysts disclosed in PCT/US10/021882 represent preferred solid acid catalysts for use in the processes of the invention. The AlPO catalysts ($AlPO_4$ or AlPOs) with isomorphous substitutions for the aluminum ($Al^{III}$) and the phosphorus ($P^V$) ions at both atom positions at the same time, to form strong and tunable Brönsted acid sites within a single catalyst. Also, isomorphous substitutions for multiple metal atoms can be made for either the aluminum or the phosphorus ions alone (incorporating as few as two new and different strength acid sites) as well as for both $Al^{III}$ and $P^V$ in the same instance. Mono-substituted AlPO's according to PCT/US10/021882 must be substantially phase pure and have at least one aluminum, ($Al^{III}$), site substituted by a divalent ion ($M^{II}$) or at least one phosphorus, ($P^V$), site substituted by a tetravalent ion ($M^{IV}$). In the mono-substituted AlPOs of the invention, the $Al^{III}$ or the $P^V$ sites may each be multiply substituted with two or more such ions. Elements which form divalent ions or tetravalent ions may be used for these substitutions. In the processes of the invention, $M^{II}$ may be, but is not limited to, $Zn^{II}$, $Mg^{II}$, $Mn^{II}$, $Co^{II}$, $Ca^{II}$, $Ni^{II}$, $Pd^{II}$, and mixtures thereof and $M^{IV}$ may be, but is not limited to, $Si^{IV}$, $Zr^{IV}$, $Pt^{IV}$, $Sn^{IV}$, $Ti^{IV}$, $Ge^{IV}$, $Pd^{IV}$, and mixtures thereof. The isomorphously substituted AlPO catalysts used in the process of the invention may be prepared as described in PCT/US10/021882.

The temperature that may be employed in an alcohol to olefin conversion process of the invention may vary over a wide range depending, at least in part, on the selected non-volatile acid catalyst. In general, the process can be conducted at an effective temperature ranging between about 23° C. and the critical temperature of the alcohol. Preferably between 100° C. and the critical temperature and more preferably between 150° C. and the critical temperature. Temperatures outside the stated range are not excluded from the scope of this invention, although such do not fall within certain desirable embodiments of the invention. At the lower end of the temperature ranges and, thus, generally at the lower rate of reaction, the formation of the desired light olefin products may become markedly slow. Notwithstanding these factors, the reaction will still occur and the feedstock, at least in part, can be converted to the desired light olefin products at temperatures outside the ranges stated above for a process of the invention.

An alcohol to olefin conversion process of the invention is effectively carried out over a wide range of pressures including autogenous pressures. At pressures ranging between about 0.10 atmospheres and about 500 atmospheres, such as, for example, between about 1 atmosphere and about 100 atmospheres, and further such as, for example, between about 1 atmosphere and about 30 atmospheres, the formation of light olefin products will be affected although the optimum amount of product will not necessarily form at all pressures. The pressures referred to herein for the process are exclusive of the inert diluent, if any is present, and refer to the partial pressure of the feedstock as it relates to oxygenates or mixtures thereof. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum although light olefin products can be formed.

An alcohol to olefin conversion process of the invention is affected for a period of time sufficient to produce the desired light olefin products. In general, the residence time employed to produce the desired product can vary from seconds to a number of hours. It will be readily appreciated by one skilled in the art that the residence time will be determined to a significant extent by the reaction temperature, the non-volatile acid catalyst selected, the WHSV, the phase (liquid or vapor) selected, and, perhaps, selected process design characteristics.

An alcohol to olefin conversion process of the invention may be carried out under process conditions comprising a temperature ranging between about 100° C. and 300° C., but not above the critical temperature of the alcohol using a pressure ranging between about 1 atmosphere to about 30 atmospheres and more preferably between 2 and 25 atmospheres. The temperature, pressure, and WHSV are each selected such that the effective process conditions, i.e. the effective temperature, pressure, and WHSV, are employed in conjunction, i.e., correlated, with the selected non-volatile acid catalyst and selected oxygenate feedstock such that light olefin products are produced.

The oxygenate feedstock is selected based on the olefin to be produced. Generally speaking, the feedstock is the corresponding alcohol (linear, branched, substituted, etc.), e.g., ethanol to produce ethylene, propanols to produce propylenes, butanols to butenes, etc. The preparation of the oxygenate feedstock is known in the art.

Ideally, the feedstock should be 'dry', but especially when the reaction is carried out in the liquid phase, under conditions where the product is a gas, may contain substantial amounts of water but, of course, not so much as to adversely impact the catalytic dehydration. In addition to the presence of alcohols (e.g., ethanol, propanol, butanols, etc.), or mixtures thereof in the feedstock, a diluent may be present in the feedstock in an amount ranging between about 1 and about 99 mole percent, based on the total number of moles of all feed components fed to the reaction zone (or catalyst). Typical of the diluents which may be employed in the process are, for example, helium, argon, nitrogen, carbon monoxide, carbon dioxide, hydrogen, water (steam), paraffins, hydrocarbons (such as methane and the like), aromatics (such as benzene, toluene, xylenes and the like), mixtures thereof, and the like. Various feedstocks and their preparation as well as processes using them are described, for example, in U.S. Pat. No. 7,626,067 and published PCT applications WO 03/000412 and WO 03/000413. It has been discovered that the addition of a diluent to the feedstock prior to such being employed in the process is generally beneficial, although not required.

An alcohol to olefin conversion process of the invention may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such non-volatile catalysts in series to provide for a desired product mixture. Owing to the nature of the process, it may be desirable to carry out the process by use of the catalyst in a dynamic (e.g., fluidized or moving) bed system or any system of a variety of transport beds rather than in a fixed bed system. Such systems would readily provide for any regeneration (if required) of the catalyst after a given period of time. If regeneration is required, the catalyst can be continuously introduced as a moving bed to a regeneration zone where it can be regenerated, such as for example by removing carbonaceous materials by oxidation in an oxygen-containing atmosphere In the preferred practice of the invention, if coking occurs, the catalyst will be subject to a regeneration step by burning off carbonaceous deposits accumulated during reactions.

Reactions where a solid catalyst phase and liquid and gaseous reactant and product phases are present are termed three phase reactions. Three phase reactions may be carried out in any type of convenient equipment: a simple boiling reactor, a trickle bed reactor (either massive or with solid acid catalyst deployed in tubes) or even a distillation column. In the latter case, a non-volatile catalyst may function as the distillation packing or may be present in discrete reaction zones within the distillation and be applied in combination with trays or other distillation packing.

A single stage (from a volatilization standpoint) back-mixed (from a reaction standpoint) boiling reactor is conveniently employed where a volatile product is produced from a less volatile precursor. These reactors are especially useful in practicing the invention where a liquid phase non-volatile acid such as sulphuric acid, p-toluenesulfonic acid, methanesulfonic acid, heteropoly acids or phosphoric acid is the catalyst, but may also be employed with a solid phase catalyst present as a slurry in the liquid phase. The reactor may be mechanically agitated or the volatilization of the products may supply sufficient agitation. Heat of reaction and vaporization may be supplied by a heat transfer surface inside the reactor or by circulating a fraction of the reactor contents through an external heat exchanger. Fresh feed, which may be pre-heated, may be added directly to the reactor or to the external heat exchanger loop or to any stream of recovered unconverted alcohol being recycled from downstream.

A simple boiling reactor may also be used when the catalyst is a solid, but three phase reactions are more conveniently carried out in a trickle bed reactor. Trickle bed reactors are well known in the art. See, for example: Al-Dahhan, M., et. al., High pressure Trickle Bed Reactors—A Review, IEC Research 1997 36 3292-3314. The trickle bed reactor may be operated in countercurrent or co-current flow, but co-current flow is preferred. Better catalyst wetting is obtained in downflow and this is therefore preferred.

In order for a trickle bed reactor to perform adequately, the catalyst particles should be wetted by the liquid phase. Operationally one controls this wetting by controlling the relative flow rates of gas and liquid (G/L). Molar G/L ratio is preferably between 0.1 and 10 and preferably between 0.5 and 2.0. As known in the art, a convenient way to independently control G/L is to recycle liquid phase reactor effluent to the inlet.

Whatever type of reactor is employed, a gas phase product is withdrawn. The net olefin product is preferably contained within this gas phase effluent. A liquid phase effluent from the reaction zone may also be withdrawn. In the case of a trickle bed reactor, this liquid phase product co-exists with the gas phase product throughout the reactor and they may be withdrawn together. In the case of a single stage boiling reactor, the liquid phase product may be withdrawn from the reactor or from its external heating loop.

Water produced by the reaction, i.e. one molecule per molecule of olefin, plus any water present in the alcohol feed, must be withdrawn from a continuous reactor, either as part of the vapor phase product or as a component of the liquid phase effluent. Additionally any undesired by-products, such as ethers or heavy by-products must be withdrawn as components of the vapor or liquid effluents. Spent catalyst may also be withdrawn from a single stage back-mixed boiling reactor as a component of its liquid phase effluent.

The reaction process of the invention has been described with reference to the dehydration of alcohols to form olefins. The reaction process of the invention may also be used in reactions such as the hydrolysis of olefins to alcohols, esterification, transesterification, polymerization, aldol condensation and ester hydrolysis, where the reaction pressure is greater than atmospheric pressure and the reaction temperature is above the boiling point of at least one reaction product at reaction pressure, but below the critical temperature of at least one reactant, and at least one reaction product is substantially in the gaseous phase. An olefin hydrolysis reaction takes an olefin reactant and converts it to an alcohol product, for example, ethylene to ethanol and propylene to propanol. Esterifications include, for example, the reaction of light alcohols (reactant) with acids to make the corresponding esters (product). Examples of estrifications include reaction of methanol and ethanol, respectively with acetic acid to make methyl and ethyl acetates respectively; reaction of acrylic and methacrylic acids with lower alcohols like methanol and butanol to make methyl acrylate, methyl methacrylate, and butyl methacrylate; and the reaction of 2-ethyl hexanol with phthalic anhydride to make dioctyl phthalate. An ester hydrolysis of interest converts an ester reactant to an alcohol product, for example, the hydrolysis of methyl acetate (reactant) to methanol (product) and acetic acid. Transesterifications include the conversion of one ester (reactant) to a product ester, for example, conversion of methyl methacrylate to butyl methacrylate and conversion of alkyl glycerates to methyl esters (biodiesel) and glycerin. Aldol condensation convert aldehydes or ketones to higher molecular weight hydroxyl aldehydes or ketones. Polymerization, for example, converts olefins to oligomers or alcohols and esters to polyesters.

Accordingly, the invention also relates to catalytic processes for the conversion of an alcohol, an olefin, an aldehyde, a ketone or an ester. The catalytic process is a hydrolysis of an olefin to an alcohol, an esterification, a transesterification, a polymerization, an aldol condensation or an ester hydrolysis. The catalytic process continuously flows through a reaction zone a liquid phase containing an alcohol, an olefin, an aldehyde, a ketone or an ester to contact a non-volatile acid catalyst at a reaction temperature and pressure to at least partially convert the an alcohol, an olefin, or an ester in the liquid phase to a corresponding reaction product. The reaction pressure is greater than atmospheric pressure and the reaction temperature is above the boiling point of at least one reaction product at reaction pressure, but below the critical temperature of the alcohol, olefin, aldehyde, ketone or ester, and the reaction product is substantially in the gaseous phase. The process then separates the reaction product-containing gaseous phase from the liquid phase.

EXAMPLES

Example 1

This example illustrates conversion of ethanol to ethylene in a trickle bed reactor, using an isomorphously substituted AlPO catalyst. FIG. 1 shows a process configuration for dehydration of ethanol using a trickle bed reactor. A $Mg^{II}Si^{IV}$ ALPO-5 catalyst such as in Example 7 of PCT/US10/021882, filed Jan. 22, 2010, (incorporated herein by reference), by reacting phosphoric acid with aluminum hydroxide followed by slowly adding magnesium acetate (as the tetrahydrate). The mixed solution of precursors was then mixed with fumed silica, before adding methyldicyclohexylamine as structure directing agent. More water was added and the resultant gel was aged before heating for two hours at 180° C. under autogenous pressure. After quench, filtration and aqueous wash, the product was dried at 90° C. before calcination, for two hours under nitrogen and 12 hours under air at 550° C.

A 13 foot diameter by 80 ft. (tangent-to-tangent) reactor vessel is loaded with 64000 gallons of the isomorphously substituted ALPO catalyst so prepared, configured into two 32 foot deep beds with internal liquid flow redistribution. Reaction pressure is 20 atm. Inlet and outlet temperatures are 185° and 175° C. respectively.

Fresh ethanol/water azeotrope feedstock containing 15,640 lbs/hr of ethanol is pumped to just above reactor pressure and mixed with recycled ethanol/water azeotrope from the ethanol recovery column and with heated recycled liquid from the reactor flash drum. This mixed stream is fed to the top of the reactor. Vapor to liquid ratio at the exit of the trickle bed is 0.5 molar.

Reactor effluent is flashed to approximately 17 atm. The liquid phase is heated and recycled to the reactor. The gas phase containing ca. 9100 lbs/hr of ethylene product at a 5 mol % concentration is fed to a quench system and then, without further compression into a conventional ethylene purification train.

Quench bottoms are fed to an ethanol-water distillation column where net water of reaction plus what was contained in the net feed is rejected. Recovered ethanol-water azeotrope is returned to the reactor.

Example 2

The same reaction system equipment and catalyst is used for dehydration of n-propanol to propylene, except that reaction pressure at 175° C. is about 10 atm. A 5% concentration of olefin is again obtained. Net production is ca. 13,650 lbs./hr of propylene from 20,400 lbs/hr of propanol feed as the water azeotrope. (43 mol % propanol)

Example 3

This example illustrates the use of ZSM-5 for conversion of ethanol to ethylene.

ZSM-5 catalyst is prepared and converted to its acid form (HZSM-5) as described in Phillips and Datta (IEC Res 1997 36 4466-4475). The same trickle bed reactor is employed as in Example 1. In order to maintain the same vapor phase composition, however, throughput is adjusted to 3120 lbs/hr of fresh ethanol (as the ethanol water azeotrope) and net ethylene production is 1820 lbs/hr.

Example 4

This example illustrates conversion of ethanol to ethylene in a single stage backmixed boiling reactor. A 2.0 liter zirconium lined reactor set in a heating mantle is charged with concentrated sulfuric acid and brought to 180° C. Ninety millimoles per hour of liquid ethanol containing ca. 5 mol % water is fed continuously to the flask. Pressure is allowed to rise to 20 atmospheres before gas is withdrawn at a rate of 100 millimoles per hour. At steady state, the gas phase composition is 85 vol % ethanol, 10 vol % water and 5 vol % ethylene.

The boiling reactor was set up with a catalyst bed height of 5 cm with <0.5 cm of glass beads below the catalyst and glass beads above the catalyst up to just below the gas inlet. The masses of catalyst used are shown in Table 2, below. Three runs were done at different temperatures.

TABLE 2

Masses of catalyst used.

| % Water | Mass of catalyst |
|---------|------------------|
| 25      | 0.3658           |
| 50      | 0.3579           |
| 75      | 0.3362           |

The catalyst was a MgAlPO-5 catalyst (disclosed in PCT/US10/021882) with 4% metal loading in the gel. The reaction was carried out under 50 ml/min He carrier gas and an ethanol/water flow rate of 30 µl/min. The reactor was allowed to a reach temperature of 250, 275 or 300° C. and then allowed to equilibrate for 2 hours before samples were taken. These were calculated based on the gaseous samples only. This is due to there being no internal standard and therefore the data from the liquid samples was very dependent on the amount of sample injected into a gas chromatograph (GC).

The data suggest water does not have a detrimental effect on the catalyst performance. This is particularly evident in the conversions at 275 and 300° C. where a slight increase is observed with greater water content in the feedstock. It is likely the 250° C. 50% water point is an anomaly.

In general the selectivity data show increased selectivity with increasing reaction temperature. However, if the 300° C. data going from 25 to 50% water is considered, this still gives a selectivity of greater than 90% despite doubling the water content.

The claimed invention is:

1. A catalytic process for the conversion of an alcohol, an olefin, an aldehyde, a ketone or an ester comprising the steps of:
    continuously flowing through a reaction zone selected from a trickle bed reaction zone or a boiling reactor zone a liquid phase containing an alcohol, an olefin, an aldehyde, a ketone or an ester to contact a non-volatile acid catalyst at a reaction temperature and pressure to at least partially convert the alcohol, olefin, or ester in the liquid phase to corresponding reaction product,
        wherein the reaction pressure is greater than atmospheric pressure and the reaction temperature is above the boiling point of at least one reaction product at reaction pressure, but below the critical temperature of the alcohol, olefin, aldehyde, ketone or ester, and the reaction product is substantially in the gaseous phase; and
        wherein the catalytic process is a hydrolysis of an olefin to an alcohol, an esterification, a transesterification, a polymerization, an aldol condensation; dehydration of an alcohol to an olefin or an ester hydrolysis; and
    separating said reaction product-containing gaseous phase from the liquid phase.

2. The catalytic process of claim 1, further comprising the steps of:
    recovering at least a portion of the liquid phase as a reaction effluent;
    optionally recovering any unconverted alcohol, olefin, or ester from the gaseous phase or from the reaction effluent; and
        optionally recycling any unconverted alcohol, olefin, or ester to the reaction zone.

3. A catalytic process of claim 1 wherein the reaction conditions comprise a reaction pressure which is greater than 10 atm.

4. A catalytic process of claim 1 wherein the reaction conditions comprise a reaction pressure which is greater than 20 atm.

5. A catalytic process of claim 1 wherein the reaction conditions comprise a reaction pressure which is greater than 30 atm.

6. A catalytic process of claim 1 wherein the separating step comprises removing gas phase reaction product from liquid phase alcohol, olefin, aldehyde, ketone or ester in the reaction zone.

7. A catalytic process of claim 1 where reaction zone is a trickle bed reaction zone.

8. A catalytic process of claim 7 where the Weight Hourly Space Velocity (WHSV) is between 0.1 and 10.

9. A catalytic process of claim 7 where the reaction zone has a gas/liquid ratio of between 0.1 and 5.

10. A catalytic process of claim 1 where the reaction zone is a boiling reactor zone.

11. A catalytic process of claim 1 comprising the steps of:
    recovering at least a portion of the liquid phase as a reaction effluent;
    recovering any uncoverted alcohol, olefin, aldehyde, ketone or ester from the gaseous phase or from the reaction effluent; and
    recycling any unconverted alcohol, olefin, aldehyde, ketone or ester to the reaction zone.

12. The catalytic process of claim 1, wherein the non-volatile acid catalyst is a solid acid catalyst.

13. The catalytic process of claim 12, wherein the non-volatile acid catalyst is an AlPO catalyst.

14. The catalytic process of claim 1, wherein an olefin, an aldehyde, a ketone or an ester is flowed through the reaction zone.

15. The catalytic process of claim 12, wherein an olefin, an aldehyde, a ketone or an ester is flowed through the reaction zone.

16. The catalytic process of claim 13, wherein an olefin, an aldehyde, a ketone or an ester is flowed through the reaction zone.

* * * * *